US008071108B2

(12) United States Patent
Beer et al.

(10) Patent No.: US 8,071,108 B2
(45) Date of Patent: Dec. 6, 2011

(54) PESTIVIRUS MUTANT FOR USE IN A VACCINE

(75) Inventors: Martin Beer, Greifswald-Insel Riems (DE); Ilona Reimann, Greifswald-Insel Riems (DE); Patricia Koenig, Greifswald-Insel Riems (DE)

(73) Assignee: Intervet International B.V., Boxmeer (NL)

( * ) Notice: Subject to any disclaimer, the term of this patent is extended or adjusted under 35 U.S.C. 154(b) by 53 days.

(21) Appl. No.: 12/441,169

(22) PCT Filed: Sep. 20, 2007

(86) PCT No.: PCT/EP2007/059923
§ 371 (c)(1),
(2), (4) Date: Mar. 13, 2009

(87) PCT Pub. No.: WO2008/034857
PCT Pub. Date: Mar. 27, 2008

(65) Prior Publication Data
US 2009/0232846 A1    Sep. 17, 2009

Related U.S. Application Data

(60) Provisional application No. 60/846,662, filed on Sep. 22, 2006.

(30) Foreign Application Priority Data

Sep. 22, 2006    (EP) ..................................... 06121147

(51) Int. Cl.
*A61K 39/12*    (2006.01)
(52) U.S. Cl. .................................................. 424/218.1
(58) Field of Classification Search ................ 424/218.1
See application file for complete search history.

(56) References Cited

U.S. PATENT DOCUMENTS 7,572,455 B2 *    8/2009    Meyers et al. ............. 424/218.1

FOREIGN PATENT DOCUMENTS

| EP | 1 013 757 A2 | 6/2000 |
|----|--------------|--------|
| EP | 1 161 537 | 10/2006 |
| WO | WO 2005/111201 | 11/2005 |

OTHER PUBLICATIONS

Gil et al, Journal of Virology, Jan. 2006, vol. 80, No. 2, pp. 900-911.*
Kupefermann et al, Journal of Virology, 1996, vol. 70, No. 11, pp. 8175-8181.*
Zemke et al, Veterinary Microbiology, 2010, vol. 142, pp. 69-80.*
Mischkale et al, Veterinary Microbiology, 2010, vol. 142, pp. 3-12.*

Behrens, et al., "Characterization of an Autonomous Subgenomic Pestivirus RNA Replicon", Journal of Virology, vol. 72, No. 3, pp. 2364-2372 (Mar. 1998).
Fletcher, et al., "The influence of viral coding sequences on pestivirus IRES activity reveals further parallels with translation initiation in prokaryotes", RNA, vol. 8, No. 12, pp. 1558-1571 (Dec. 2002).
Kupfermann, et al., "Bovine Viral Diarrhea: Characterization of a Cytopathogenic Defective Interfering Particle with Two Internal Deletions", Journal of Virology, vol. 70, No. 11, pp. 8175-8181 (1996).
Lai, et al., "Generation and Characterization of a Hepatitis C Virus NS3 Protease-Dependent Bovine Viral Diarrhea Virus", Journal of Virology, vol. 74, No. 14, pp. 6339-6347 (Jul. 2000).
Mayer, et al., "Attenuation of classical swine fever virus by deletion of the viral $N^{pro}$ gene", Vaccine, vol. 22, No. 3-4, pp. 317-328 (Jan. 2004).
Moser, et al., "Cytopathogenic and Noncytopathogenic RNA Replicons of Classical Swine Fever Virus", Journal of Virology, Vo. 73, No. 9, pp. 7787-7794 (Sep. 1999).
Myers, et al., "Efficient Translation Initiation Is Required for Replication of Bovine Viral Diarrhea Virus Subgenomic Replicons", Journal of Virology, vol. 75, No. 9, pp. 4226-4238 (May 2001).
Tautz, et al., "Establishment and Characterizatin of Cytopathogenic and Noncytopathogenic Pestivirus Replicons", Journal of Virology, vol. 73, No. 11, pp. 9422-9432 (Nov. 1999).
Tratschin, et al., "Classical Swine Fever Virus Leader Proteinase $N^{pro}$ Is Not Required for viral Replication in Cell Culture", Journal of Virology, vol. 72, No. 9, pp. 7681-7684 (Sep. 1998).
PCT International Search Report dated Dec. 4, 2007 for corresponding PCT Application No. PCT/EP2007/059923.
Hoffman, B. et al., "A Universal Heterologous Internal Control System for Duplex Real-Time RT-PCR Assays Used in a Detection System for Pestiviruses" (Abstract), Journal of Virological Methods, 136(1-2):200-209, (Sep. 2006).
Maurer, Roland et al., "Oronasal Vaccination with Classical Swine Fever Virus (CSFV) Replicon Particles with Either Partial or Complete Deletion of the E2 Gene Induces Partial Protection Against Lethal Challenge with Highly Virulent CSFV", Vaccine, 23:3318-3328, (2005).
Meyers, Gregor et al., "Recovery of Cytopathogenic and Noncytopathogenic Bovine Viral Diarrhea Viruses from cDNA Constructs", Journal of Virology, 70(12):8606-8613 (Dec. 1996).
Wolfmeyer, A. et al., "Genomic (5'UTR) and Serological Differences Among German BVDV Field Isolates", Archives of Virology, 142:2049-2057, (1997).

* cited by examiner

*Primary Examiner* — Ali R. Salimi
(74) *Attorney, Agent, or Firm* — William M. Blackstone

(57) ABSTRACT

The present invention comprises new pestivirus mutants, characterized in that the mutants are based on a cp strain of the virus wherein part of the gene sequence encoding the Npro region is deleted, except that the deleted part does not encompass the coding sequence for the N-terminal twelve amino acids of the Npro protein. Preferably the pestivirus is the Bovine Viral Diarrhea Virus (BVDV). It was found that a mutant according to the invention is a safe and efficient vaccine candidate.

9 Claims, 8 Drawing Sheets

Construction of CPΔNpro

Mean leukocyte values after vaccination and challenge infection

Figure 7
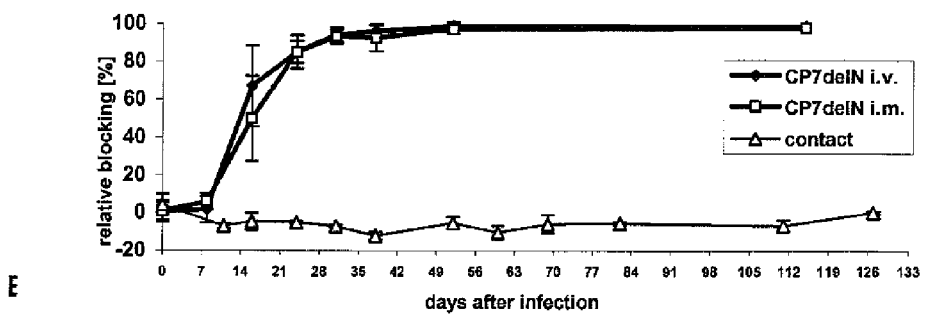
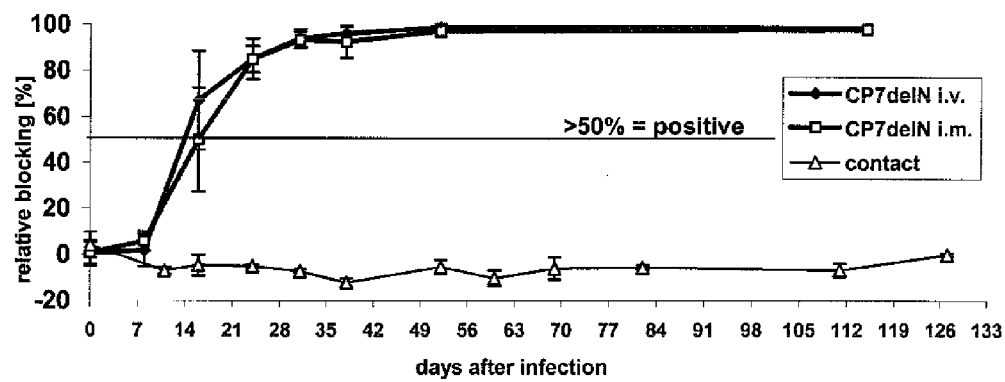

Figure 8

Mean leukocyte counts after CP7 ΔNpro inoculation (trial II)

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: cloning primer cp7-208-XhoI

<400> SEQUENCE: 1
aagcctcgag atgccacgtg g                                           21

<210> SEQ ID NO 2
<211> LENGTH: 46
<212> TYPE: DNA
<213> ORGANISM: Artificial Sequence
<220> FEATURE:
<223> OTHER INFORMATION: Cloning primer cp7-406R-PacI

<400> SEQUENCE: 2
tctaggtatc cagttaatta atgttttgta taaaagttca tttgtg                46

<210> SEQ ID NO 3
<211> LENGTH: 37
<212> TYPE: DNA
<213> ORGANISM: Artificial Sequence
<220> FEATURE:
<223> OTHER INFORMATION: Cloning primer cp7-873-PacI

<400> SEQUENCE: 3
taccttaatt aactccgaca caaaagatga aggggtg                          37

<210> SEQ ID NO 4
<211> LENGTH: 23
<212> TYPE: DNA

```
<213> ORGANISM: Artificial Sequence
<220> FEATURE:
<223> OTHER INFORMATION: cp7-4913R

<400> SEQUENCE: 4
ccgtggcggc cgcatttagg gca                                          23

<210> SEQ ID NO 5
<211> LENGTH: 12
<212> TYPE: PRT
<213> ORGANISM: Bovine Viral Diarrhea Virus (BVDV)

<400> SEQUENCE: 5

Met Gln Leu Ile Thr Asn Gln Leu Leu Tyr Lys Thr
1               5                   10
```

PESTIVIRUS MUTANT FOR USE IN A VACCINE

PRIORITY CLAIM TO RELATED PATENT APPLICATIONS

This patent claims priority under 35 U.S.C. §371 as a national phase of International Patent Application No. PCT/EP2007/059923 (filed Sep. 20, 2007; and published on Mar. 27, 2008, as International Publication No. WO 2008/034857), which, in turn, claims priority to European Patent Application No. 06121147.00 (filed Sep. 22, 2006) and U.S. Application No. 60/846,662 (filed Sep. 22, 2006). The entire text of each of the above-referenced patent applications is hereby incorporated by referenced into this patent.

The present invention relates to a mutant of a pestivirus, said mutant expressing all structural proteins of the pestivirus, its use in a vaccine to protect life stock against infection with a pestivirus, as well as to a vaccine comprising said mutant.

Animals may be protected against pestiviruses by vaccination, however, conventional inactivated or modified live vaccines have disadvantages concerning safety as well as efficacy. Therefore, new types of vaccines should be developed.

Pestiviruses can be divided into two different biotypes, cytopathogenic (cp) and non cytopathogenic (ncp) viruses, respectively. Bovine viral diarrhea virus (BVDV), a member of the genus pestivirus within the family Flaviviridae is the causative agent of bovine viral diarrhea, an economically important disease of cattle world-wide. Genetically and structurally closely related virus species are Classical Swine Fever Virus (CSFV) and the ovine Border Disease Virus (BDV). Pestiviruses can induce severe diseases with marked economical losses world wide. The major economic losses caused by BVDV infections are reduced fertility, abortions and the generation of persistently infected calves, which can develop fatal "Mucosal Disease". The pestivirus genome consists of a single-stranded RNA of positive orientation. The RNA has a length of approximately 12.3 kb and contains one large open reading frame (ORF), which is flanked by non-translated regions (NTR) at both genome ends. The pestiviral ORF is translated into one polyprotein, which is co- and post-translationally processed into 12 mature proteins by viral and cellular proteases. In cp BVDV NS3 is more efficiently expressed, e.g. due to insertions allowing a more efficient cleavage of nonstructural proteins NS2 and NS3. Therefore, cp BVDV is characterized by marked higher amounts of detectable NS3 in infected cell cultures. The first protein of the pestiviral ORF is Npro (N-terminal protease). Npro is a non-structural autoprotease that cleaves itself off the rest of the ORF encoded polyprotein, and thereby creates its own C-terminus and also the correct N-terminus for the first structural protein in the ORF, the C (core) protein. Npro has no counterpart in other flaviviruses.

The C protein in the ORF is followed by the other structural proteins: $E^{RNS}$, E1, E2 (in that order). Together the capsid (C) protein and the three glycosylated envelope proteins ($E^{RNS}$, E1, E2) make up the pestiviral virion. The structural proteins are followed by the non-structural proteins (p7, NS2-NS3 and NS3, NS4A, NS4B, NS5A, and NS5B). NS3 (serine protease) and NS5 (RNA-dependant RNA polymerase activity) are directly involved in viral replication.

Pestiviruses can be classified in different ways. For BVDV different genotypes (BVDV-1 and BVDV-2) can be distinguished. In addition, two different biotypes can be distinguished following infection of cultured cells, referred to as cytopathic strains (cp) and non-cytopathic (ncp) strains. Genotypes are based on divergence in the sequence of the viral genome. Infection of the cultured cells with a cp strain leads to lysis of the cells, while infection with an ncp strain does not appear to cause any cell damage.

It is generally believed that cpBVDV strains develop from ncpBVDV strains by rearrangement of the viral genome. For BVDV, in ncp isolates mainly unprocessed NS2-NS3 is observed, while low amounts of NS3 are detectable. In contrast, in cp isolates the C terminal part of NS2-3 appears in higher amounts, the NS3 protein. In BVDV isolate CP7, an insertion of 27 nucleotides in the NS2-coding region was demonstrated to be sufficient for mediating efficient NS2-3 cleavage, and conferring cytopathogenicity (Tautz et al., J. Virol., 73(11), 9422-9432, 1999).

The different BVDV biotypes have been associated with different disease forms. BVDV infection also has the ability to cause persistent infection (PI) in the developing fetus. When pregnant cattle, susceptible to infection, are exposed to a noncytopathic BVDV (between 42 and 110 days of gestation) a persistently infected (PI) calf can be born. Persistently infected calves are immunotolerant for the BVDV strain which infected the fetus. PI calves therefore are lifelong efficient shedders of the virus and are the most important cause of spreading of the virus in susceptible cattle world wide. This PI syndrome therefore creates a requirement for high levels of BVDV immunity from vaccines to prevent these infections.

For BVDV a subdivision can be made in BVDV-1 strains and BVDV-2 strains. BVDV-1 and -2 can be distinguished from each other by differential PCR or nucleic acid sequencing. Recently the two genotypes have been sub-divided further into sub genotypes like BVDV1a, BVDV1b, BVDV2a and BVDV 2b. More than 11 subtypes of BVDV 1 are known.

Studies on the replication of pestiviruses have been considerably facilitated by reverse genetic systems and the discovery of autonomously replicating subgenomic RNAs (replicons). (Behrens et al., J. Virol., 72, 2364-272, 1998; Meyers et al., J. Virol., 70, 8606-8613, 1996).

The minimal requirements for CSFV replication were investigated, for example, by creating defective CSFV genomes lacking the gene sequences for the structural proteins. It was found that the defective CSFV genomes still replicated and could be packaged into viral particles when introduced in SK-6 cells together with helper A187-CAT RNA (Moser et al., J. Virol., 7787-7794, 1999).

An autonomously replicating defective BVDV genome, which lacks part of the Npro gene sequence as well as the genes encoding C, $E^{ms}$, E1, E2, p7 and NS2, had been described (Behrens et al., J. Virol., 72, 2364-2372, 1998).

Kupfermann et al., created BVDV mutants from BVDV strains SD-1 and CP 13 where the first 12 amino acids of Npro were retained, but the rest was deleted, together with the structural proteins (except for AA 551-560 of the E1 protein).

It has been suggested that the 5' coding region of the Npro gene represents part of the BVDV IRES (Tautz et al, supra; Behrens et al., supra; Meyers et al., J. Virol., 75(9), 4226-4238, 2001), and is essential for replication.

The present invention aims at providing new pestivirus mutants for use in vaccines. A vaccine mainly aims at invoking an immune response. A vaccine, on the one hand, should be able to elicit a protective immune response, while, on the other hand, it should of course not invoke the (viral) disease in the inoculated animal or contact animals. The immune response induced is usually mainly directed against the envelop proteins of the virus. But, if a replicon is used from which all the structural, more particular, all the envelop protein coding sequences have been deleted, such proteins are not produced from the replicon and no immune response to these proteins is obtained. BVDV antibodies are directed against $E^{RNS}$, E2 and NS3. Neutralizing activity was predominantly demonstrated for E2-specific antibodies.

Vaccines may be based on the whole, wild type, virus, which has been inactivated (inactivated vaccines). Vaccines may also be based on a particular protein of the virus, which may be produced in vitro by recombinant DNA techniques. Usually such a protein will be an envelope protein of the virus (subunit vaccine). The present invention is concerned with a third category of vaccines, attenuated live vaccines, based on a viral mutant which does elicit a protective immune response in the host animal, but does not invoke the viral disease, due to mutations in its genome.

Pestivirus mutants where (part of) a structural gene was deleted are known in the art. For example, in EP1161537, CSFV mutants from which the Erns protein has been deleted (and complemented in trans) are described. Maurer et al., Vaccine 23, 3318-3328, 2005, described CSFV with either partial or complete deletion of the E2 protein.

It has been suggested to use Npro deletion mutants of CSFV and BVDV as vaccine candidates.

A CSFV Npro mutant was disclosed already in Tratschin et al., J. Virol., 72(9), p7681-7684, September 1998. Tratschin et al. replaced the Npro gene by murine ubiquitin sequences (the mutant was called vA187-Ubi) and concluded that the proteolytic activity of Npro (generation of the correct N-terminus of the C protein) is essential for viral replication, but that this activity can be replaced by the proteolytic activity of ubiquitin. It was found that the mutant was completely avirulent in pigs. Tratschin et al. found that no viable virus was obtained when the Npro gene was deleted and not replaced with another protease. These mutants, wherein Npro was replaced by murine ubiquitin, were also tested for use as a live attenuated vaccine (Mayer et al., Vaccine 22, 317-328, 2004), However, it was found that a mutant based on a highly virulent CSFV strain induced viraemia in inoculated pigs 7 days post vaccination. The use of a mutant based on an avirulent CSFV strain was therefore recommended.

In further research projects, the complete BVDV-Npro coding sequence was deleted, and the resulting mutant was proposed as a vaccine candidate. In EP1013757 a BVDV Npro deletion mutant, based on cytopathic strain NADL, lacking the complete Npro sequence is described. The resulting mutant was stated to be much less infectious in cell culture and replicated slow in comparison to its wild type counterpart. Its slow growth rate was suggested to confer an attenuated phenotype. Also Lai et al, J. Virol, 74(14), 6339-6347, 2000 described a BVDV Npro null mutant based on the NADL strain. It was highly defective in replication and achieved a production level at least 10 times lower than the wild type virus. It was suggested that the mutant, due to its restricted replication capacity, may be a vaccine candidate.

Due to its lack of replication however, this type of mutant may be hard to produce in sufficient quantities. Moreover it is questionable if the mutant will replicate in the target animal to an extent where it can provoke a protective immune response.

In WO2005111201 BVDV mutants are disclosed, in which deletions were made in both the Npro gene and the Erns gene. It was concluded that an Npro mutation or an Erns mutation only was not sufficient to prevent infection of the foetus in pregnant heifers. Only in double mutants, based on a BVDV type 2 strain NY93, infection of the foetus in pregnant heifers could be prevented. (the double mutant however was only tested against a type 2 challenge, be it with another type 2 strain, and not against a BVDV type 1 challenge).

The mutants tested lacked all but the N-terminal 4 amino acids of the Npro sequence.

It was noted that the mutants growth was considerably lower than for the wild type virus. To obtain better growing viruses mutants were constructed wherein either a bovine ubiquitin gene fragment or a fragment of the bovine LC3-cocidng sequence replaced the major part of the Npro gene.

The present inventors aimed at providing a pestivirus mutant that can be used in vaccines, but the genome of which still encodes and expresses all structural-, and thus all envelope-, proteins of the pestivirus.

The present inventors worked with pestivirus mutants containing mutations in the coding region for the Npro protein of the virus.

The mutants according to the present invention are characterized in that the mutant is based on a cp strain of the virus wherein part of the gene sequence encoding the Npro region is deleted, wherein said deleted part does not encompass the coding sequence for the N-terminal twelve amino acids of the Npro protein. Preferably the pestivirus is the Bovine Viral Diarrhea Virus (BVDV).

Especially for BVDV it was found that a mutant according to the invention is a safe and efficient vaccine candidate.

The mutants provide adequate protection against infection with the wild type virus and do not give rise to persistently infected calves.

The presence of the coding sequence for the remaining twelve terminal amino acids of the Npro was shown to be sufficient to allow replication of the virus. Growth kinetics were only slightly impaired, and final titers were reduced by 0.5-1.0 $\log_{10}$. Virus propagation on conventional cells was possible with titer-yields of approximately $1-5.6 \times 10^6$ $TCID_{50}$/ml.

The mutants of the invention may contain further mutations within their genomic sequence, within coding regions or within non-coding regions. Said mutations may further attenuate the virus.

However, the mutants according to the invention preferably express all structural proteins of the virus.

Mutants according to the present invention are preferably based on cp strains of the virus.

Various cp strains of BVDV are known in the art and can be used with the present invention, such as NADL, Oregon C24V, Osloss, CP7, etc. Preferably the cp 7-strain is used. The intensity of the cytopathogenic effect of the numerous cp BVDV strains is different. Some strains induce apoptosis very early after 24 to 48 h, while others need more than 72 hours to induce detectable cell damage. It is hypothesized that this is correlated with the immunogenicity: The later the cp is induced the better the immune response is evoked. As a consequence, the strain cp 7, inducing a very late cp effect was selected, to guarantee a high vaccination efficacy.

The sequence of the N-terminal twelve amino acids varies for the different isolates of BVDV. For example the sequence may be MELITNELLYKT, which is also the sequence of the N terminal twelve amino acids of the N pro protein of strain cp7.

The twelve amino acids of Npro may be directly linked to the C terminal amino acids of the C protein. In the alternative other stretches of amino acids may introduced. For example, amino acids derived from a restriction fragment used in the construction of the mutant or linking sequences.

It has been found that mutants according to the invention can be used in the manufacture of a vaccine to protect livestock against infection with a wild type pestivirus.

The invention therefore further relates to a vaccine for the protection of cattle against BVDV infection which vaccine comprises a mutant according to the invention and a pharmaceutically acceptable carrier.

Suitable carriers are known in the art. For example the mutant virus according to the invention may be lyophilized and reconstituted in a suitable physiologically acceptable salt solution, or the vaccine may contain the mutant in a ready made liquid sterile solution, further containing known carrier additives such as stabilizers etc.

Preferably the mutant is based on the CP7 BVDV strain, wherein all of the Npro gene, except for the coding sequence for the N-terminal twelve amino acids of the Npro protein, is deleted.

BRIEF DESCRIPTION OF THE FIGURES

FIG. 7: Development of BVDV specific antibodies in animal trial II as measured with BVDV NS3 blocking ELISA FIG. 8: Mean leukocyte counts after vaccination (trial II).

EXAMPLES

Example 1

Construction of a BVDV Npro Deletion Mutant

Figure 1:
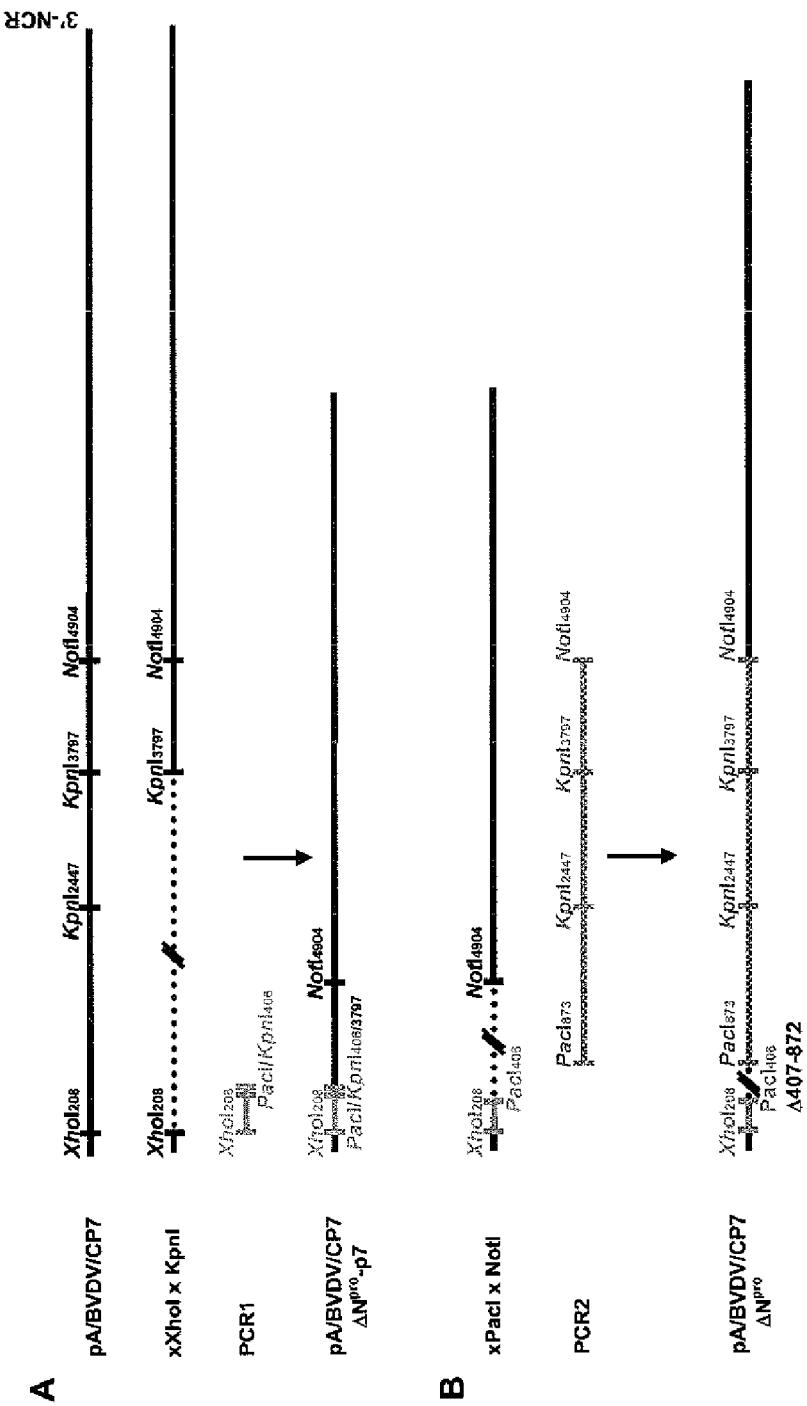
FIG. 1: Construction of BVDV Npro deletion mutant.

The BVDV cDNA clone CP7ΔNpro was constructed on the basis of the full-length infectious clone pA/BVDV (Meyers et. al., 1996) in a two step procedure. In the first step, a PCR-fragment of plasmid pA/BVDV/CP7 was amplified with the primer pair cp7_208_XhoI and cp7_406R_PacI (Table 1), digested with KpnI and XhoI and subsequently ligated into the Kpn/2447/3797 and XhoI208 digested plasmid pA/BVDV/CP7. In a second step, the resulting plasmid pA/BVDV/CP7ΔNpro-p7 and a PCR fragment amplified with the primers cp7_873_PacI and cp7_4913R from pA/BVDV/CP7 were cut with PacI and NotI and ligated. The deletion comprises most of Npro (nt 407-872; NCP7 sequence), whereas the first 36 nucleotides overlapping with the BVDV-IRES were not removed (FIGS. 1A and B).

TABLE 1

PCR primers used for plasmid construction

| Primer | Sequence (5' to 3') a | Genomic region (nucleotides) b |
|---|---|---|
| cp7_208_XhoI | AAGC<u>CTCGAG</u>ATGCCACGTGG [SEQ ID NO.: 1] | 204-224 (+sense) |
| cp7_406R_PacI | TCTA<u>GGTATCC</u>AG<u>TTAATTAA</u>TGTTTTGTATAAAAGTTCATTTGTG [SEQ ID NO.: 2] | 380-406 (−sense) |
| cp7_873_PacI | TACC<u>TTAATTAA</u>CTCCGACACAAAAGATGAAGGGGTG [SEQ ID NO.: 3] | 873-896 (+sense) |
| cp7_4913R | CCGTG<u>GCGGCCGC</u>ATTTAGGGCA [SEQ ID NO.: 4] | 4893-4915 (−sense) | a Restriction enzyme sites are underlined, additional nucleotides for in-frame ligation are printed in bold
b nucleotide position in BVDV-CP7 sequence Example 2

CP7 Npro Deletion Mutant as a Live Vaccine in Calves

In a first vaccination-challenge trial, it was shown that calves were completely protected from a heterologous BVDV type I challenge infection after a single intramuscular immunisation with CP7 ΔNpro. No nasal shedding of the vaccine virus was detected by virus isolation in cell culture. 1 out of 4 animals showed viremia for one day.

Immunisation induced a sterile immunity. Neither nasal virus shedding nor viremia were observed following the BVDV type I challenge infection.

Figure 2:
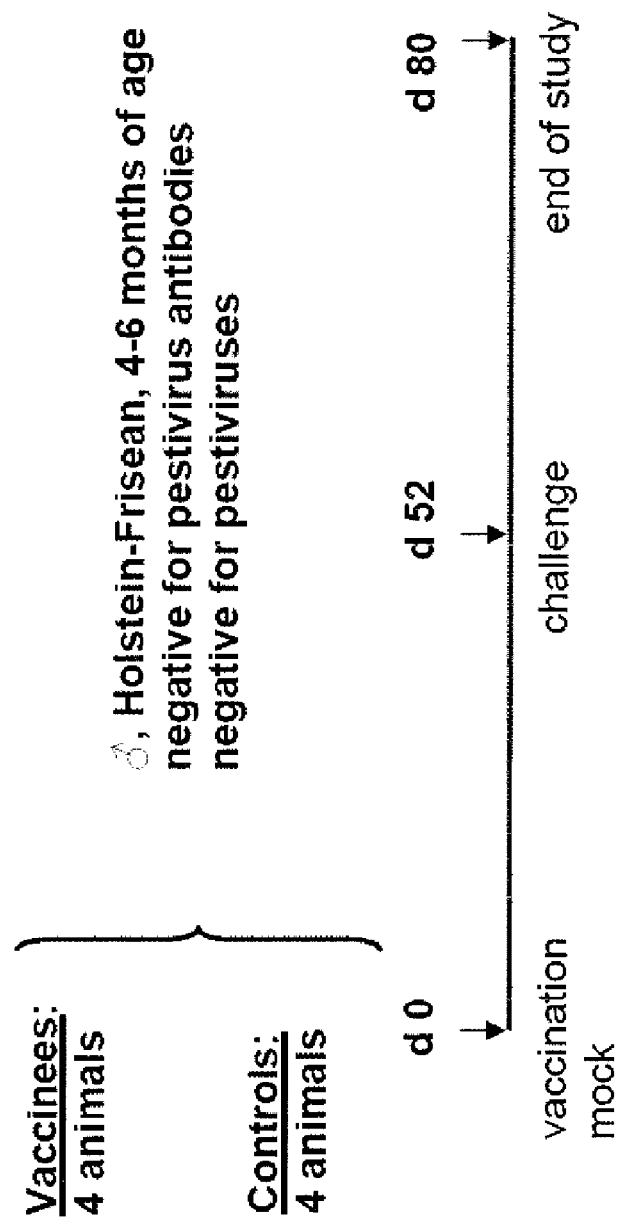
FIG. 2: Set-up of animal trial (trial I ) wherein naïve calves were vaccinated with a vaccine containing a CP7 Npro deletion mutant.

Trial Set-up:

The trial set up is illustrated in FIG. 2.

BVDV naïve calves (n=4 per group) were vaccinated or mock-vaccinated and 52 days later, a challenge infection with virulent BVDV type Ib strain SE5508 (Wolfmeyer et al., 1997) was performed. The calves were vaccinated with a single dose of 6.7 $\log_{10}$ TCID$_{50}$ BVDV CP7 ΔNpro i.m. (5 ml). For the mock vaccination an uninfected cell culture supernatant i.m. (5 ml) was used. For the challenge infection the calves received 2 ml of 6.5 $\log_{10}$ TCID$_{50}$ BVDV SE5508 (Ib) i.n., using a nebuliser.

The calves were monitored daily for clinical symptoms and body temperature was monitored daily.

For 14 days, after vaccination and after challenge infection, the calves were checked daily for viremia and nasal virus shedding.

The serological responses were monitored at weekly intervals.

Results

White blood cells were purified from EDTA-blood after alkaline lyses of erythrocytes. 100 μl of swab fluid or 3×10$^6$ leukocytes were inoculated on bovine cells in 4 parallels. After 5-6 days of co-cultivation virus replication was verified by indirect immunofluorescence testing (IIFT). One further blind passage of the supernatants was performed (6 d→IIFT).

In 1 out of 4 vaccinated calves cell bound viremia was detected. Low amounts of CP7 ΔNpro could be re-isolated on day 4 after vaccination after the first cell culture passage.

No nasal excretion of vaccine virus was recorded.

After challenge infection, no nasal shedding of BVDV SE5508 was detected in the vaccinated animals. All vaccinated animals were completely protected against viremia, and no challenge virus was re-isolated from purified white blood cells ("sterile immunity").

In contrast, all control calves exhibited nasal BVDV excretion for 6-8 days, as well as cell-bound viremia during 6-8 days.

Figure 3:
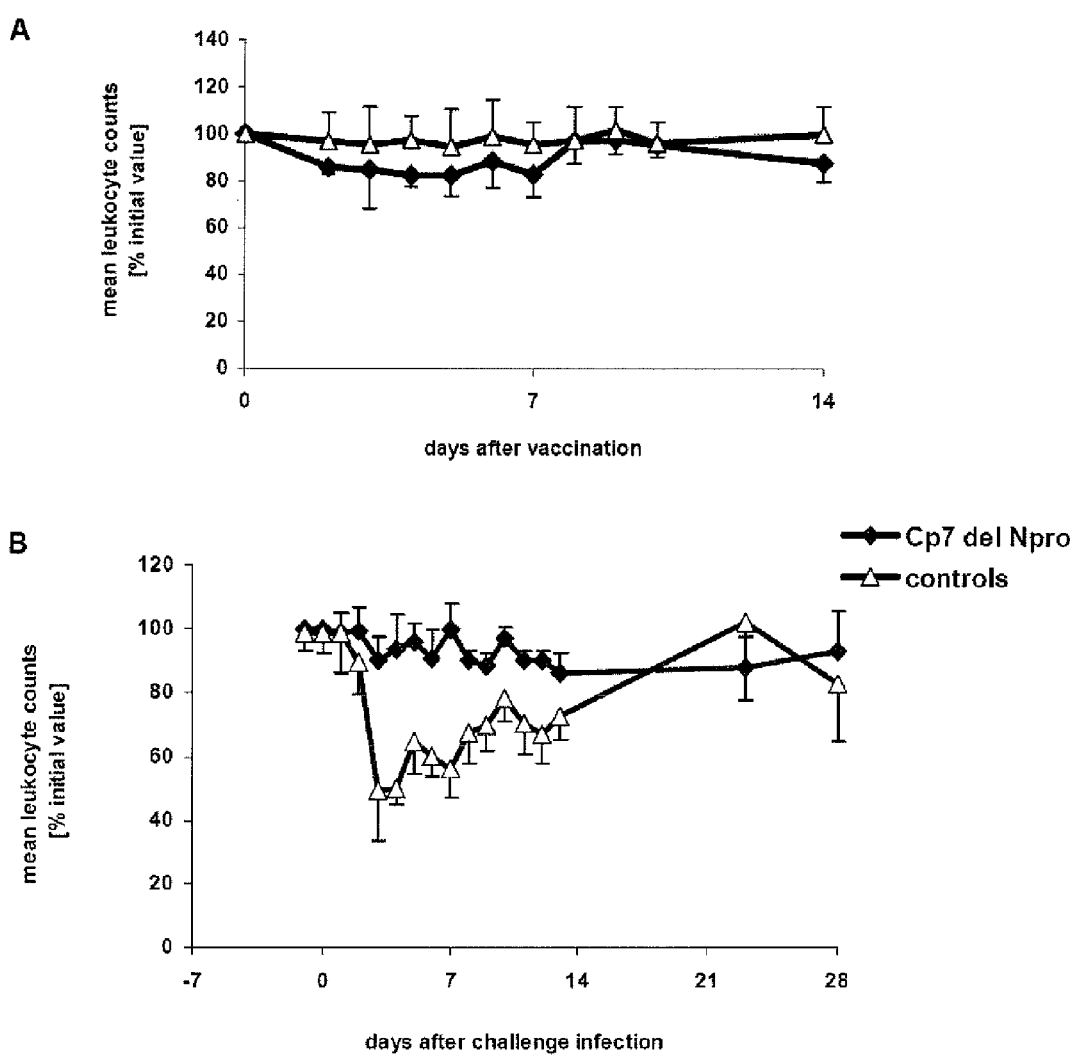
FIG. 3: Mean leukocyte counts after vaccination and challenge infection (trial I).

After vaccination all animals immunised with CP7 ΔNpro displayed a very moderate drop of the leukocyte counts with recovery to pre-vaccination values until 7 days after inoculation (FIG. 3A).

After challenge infection no significant decrease of white blood cells was observed in the immunised calves. The mean blood cell counts remained within the physiological range. In the control animals, a marked leukopenia was observed with an onset at 3 days after challenge. The average leukocyte counts stayed low for more than 2 weeks (FIG. 3B).

In comparison to the pre-vaccination temperatures, only a faint elevation of the rectal body temperatures was recorded after vaccination.

After challenge infection (c), the immunised animals showed no alterations of the temperature curves. In regard of a temperature response, the animals were clearly protected from clinical BVD.

In all control calves, a moderate raise of the temperatures occurred at 3 days after inoculation. After more than one week, body temperatures returned to the prechallenge levels.

All animals were monitored for altered general conditions and respiratory or gastrointestinal symptoms typical for BVDV.

Over the whole observation period day (4 weeks prior to immunisation until 12 weeks thereafter), mainly in the vaccinated animals, alternating mild respiratory symptoms such as nasal discharge and sporadic coughing were observed. After vaccination, no adverse clinical reactions occurred. In the vaccines, no exacerbation of the prevaccination scores was observed. After challenge infection, the immunised animals showed no clinical symptoms. In the control calves, mild respiratory symptoms were recorded and feed uptake was reduced for 1-2 days. The animals showed neither gastrointestinal disorders nor mucosal lesions.

Figure 4:
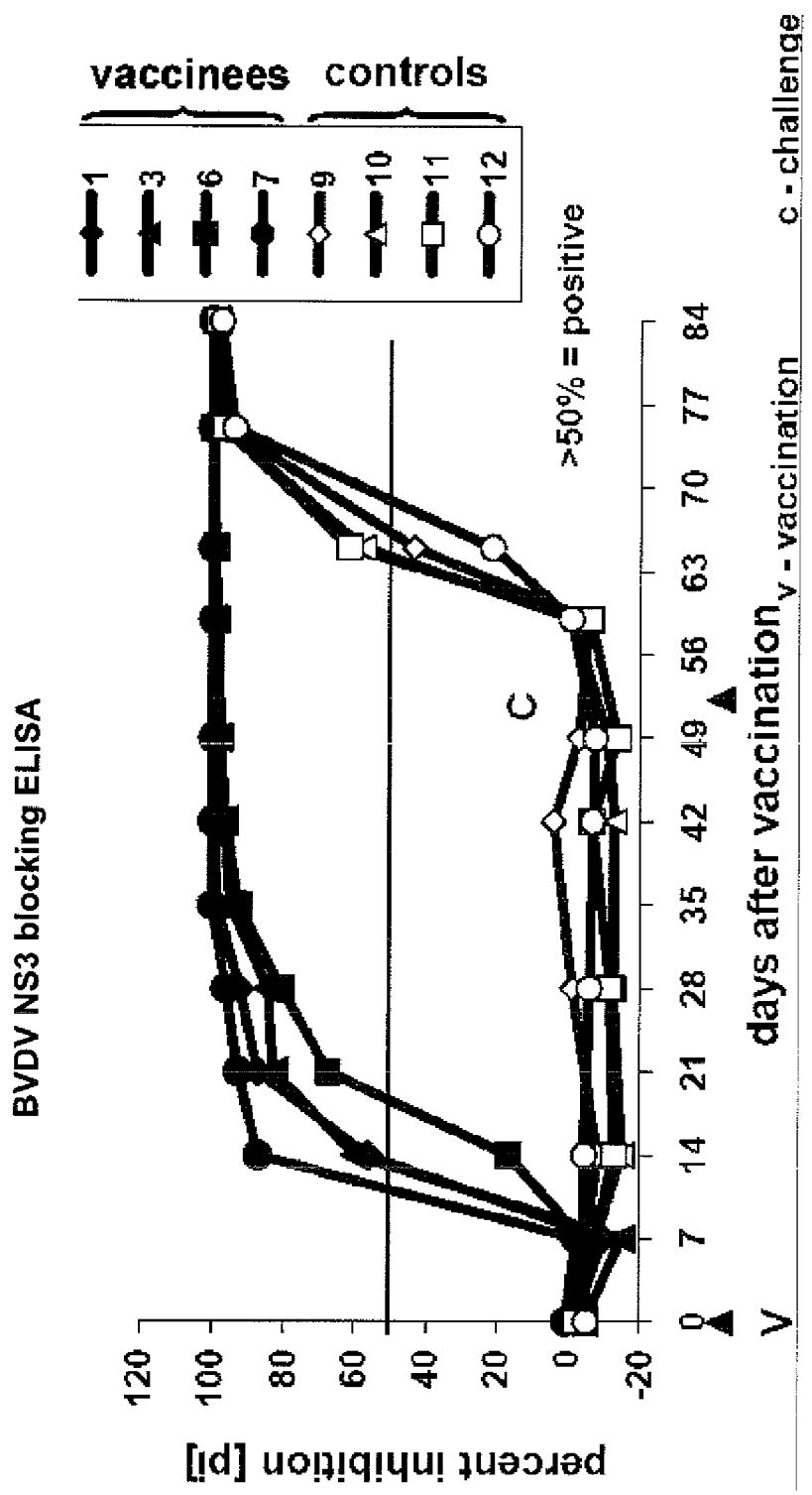
FIG. 4: Results of BVDV NS3 blocking ELISA, trial I

Serological responses of the animals were monitored using a BVDV ELISA (NS3-blocking; FIG. 4) as well as BVDV type 1 and type 2 specific neutralization assay (FIG. 5).

All animals inoculated with CP7 ΔNpro sero-converted for BVDV NS3-specific antibodies until 3 weeks after vaccination, as tested by the Ceditest BVDV ELISA (Cedi diagnostics). The control calves remained negative until 2-3 weeks after challenge infection (FIG. 4).

Figure 5:
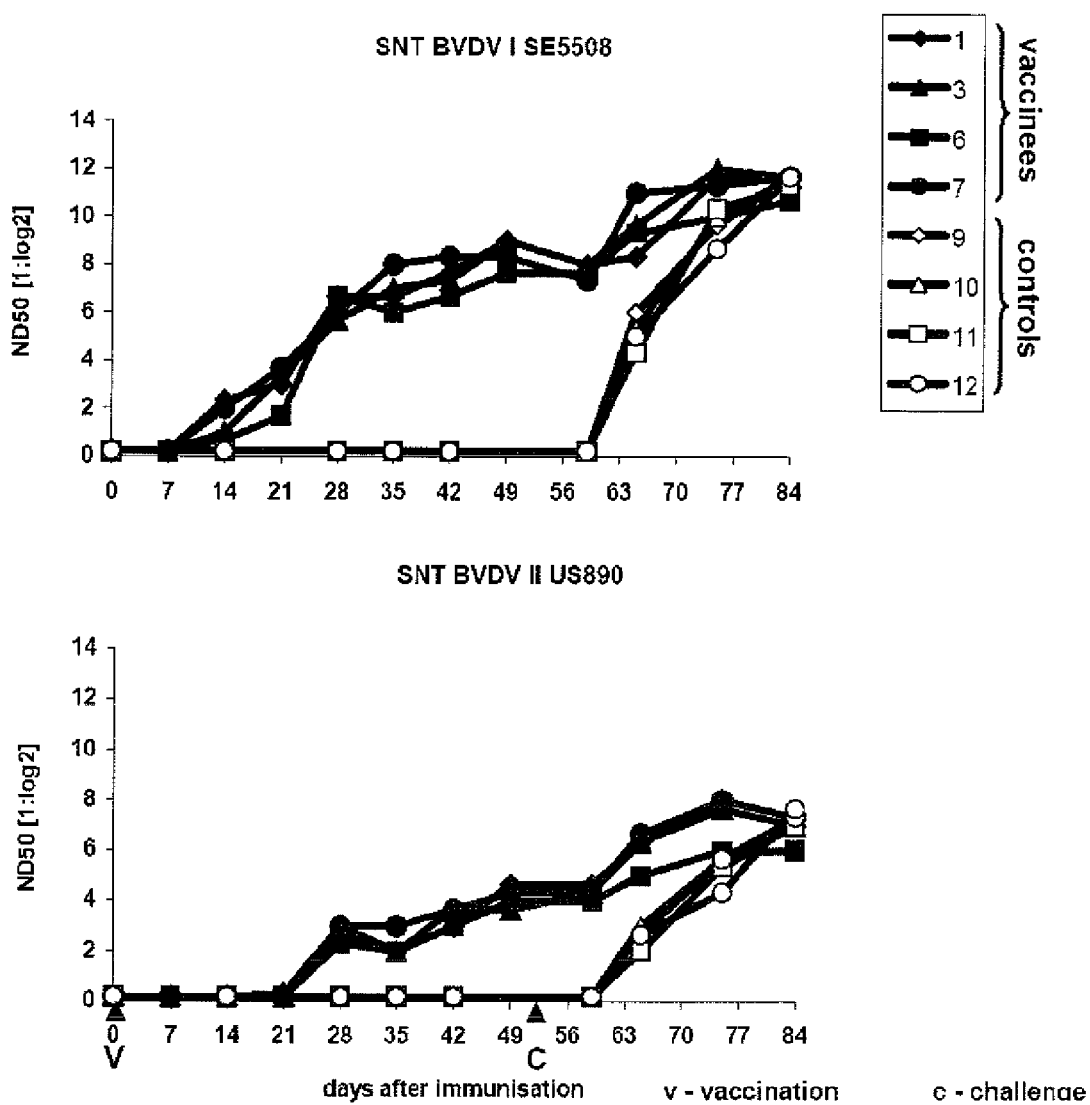
FIG. 5: Results of BVDV neutralization assay, trial I

After vaccination, all animals developed BVDV type 1 neutralising antibodies at moderate titres (FIG. 5). After challenge infection (c), the immunised animals showed no pronounced booster of the neutralising antibody titres. The mock vaccinated animals were tested negative until 2 weeks after challenge infection with BVDV type 1 strain SE5508. BVDV type 2 (strain US980) specific neutralizing antibodies at lower titres were also induced after vaccination. Neutralising antibody titres were comparable to the values of the control animals at 3 weeks after inoculation with the BVDV type I field strain SE5508.

Example 3

CP7 Npro Deletion Mutant as a Live Vaccine in Pregnant Heifers

Figure 6:
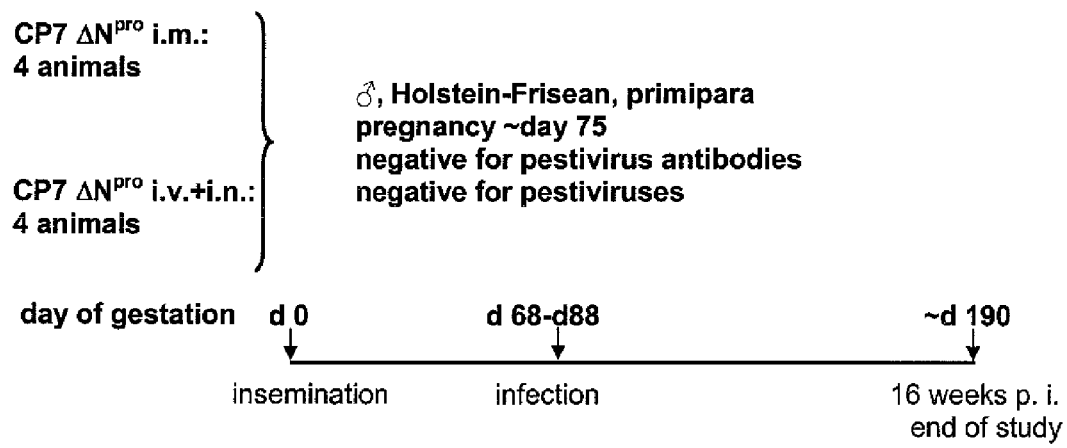
FIG. 6: Design of animal trial II wherein pregnant BVDV naïve heifers were vaccinated with CP7 Npro deletion mutant of BVDV.

The schedule of the animal trial with BVDV Npro deletion mutant strain CP7ΔNpro is depicted in FIG. 6.

BVDV naïve heifers (n=4 per group) were intramuscularly or intravenously and intranasally inoculated with the BVDV mutant strain CP7ΔNpro between day 68 and 88 of pregnancy (=first trimester).

application of 6.02 $\log_{10}$ $TCID_{50}$ BVDV CP7 ΔNpro in a 4 ml volume 3 ml i.v.+1 ml i.n.: ("worst case scenario")
4 ml i.m.: ("mimicking live vaccination")

During the trial the following parameters were monitored:
Daily:
clinical investigation
monitoring of rectal body temperatures
Daily for 10-12 days after infection:
viremia, nasal virus shedding
At weekly intervals:
serological responses
clinical abortion
fetopathogenicity
virus detection in fetal organs (exclusion of persistently infected fetuses) at 4
month after inoculation.

In addition, three Holstein-Frisean calves at an age of approximately 4 month were included as contact animals and monitored for BVDV specific antibodies in weekly intervals.

Results

For 10 to 12 days following virus inoculation, the heifers were monitored for viremia and nasal virus shedding.

100 µl of swab fluid or $3\times10^6$ purified blood leukocytes were inoculated on bovine cells in 4 parallels. After 5 to 6 days of co-culture, virus replication was verified by indirect immunofluorescence testing (IIFT) of the inoculated cultures. In addition, one additional blind passage of all supernatants was performed and tested by IIFT after 6 days of incubation.

Irrespectively of the inoculation route, no nasal virus shedding was observed. Viremia with very low viral titers could be detected at one day in 2 out of 4 animals after simultaneous intravenous and intranasal application of CP7ΔNpro and in 1 animal after intramuscular infection.

The development of BVDV-specific antibodies was monitored with a commercially available NS3-specific blocking ELISA (Ceditest BVDV ELISA; Cedi Diagnostics, The Netherlands). All inoculated animals seroconverted for NS3-specific antibodies until 2 to 3 weeks after vaccination (FIG. 7). All contact animals remained seronegative over the whole observation period, which was also confirmed by serum neutralization testing.

In both groups no marked decrease of the leukocyte counts was observed after inoculation. Mean relative blood leukocyte counts declined less than 20% with a recovery to pre-infection values within 8 days (FIG. 8). A rebound effect with increased leukocyte values was noticed for all animals with slightly elevated values until the end of the observation period after 4 weeks. After intramuscular infection, with the BVDV CP7 Npro deletion mutant, a more retarded leukocyte reduction was evident with onset at 4 days p.i. and regression at 8 d p.i. The reduction values between the 2 groups were comparable (FIG. 8).

Compared to the prechallenge body temperatures, no elevation of the rectal body temperatures was recorded after application of the Npro deletion mutant.

All animals were monitored for general conditions and BVDV-specific clinical symptoms. In all animals (inoculated animals and contact controls) unspecific mild ocular discharge was observed over the whole period. After infection no adverse reactions occurred and no clinical signs of disease were observed.

The heifers were purchased from 3 different holdings. Four of five animals originating from the same farm exhibited problems with the musculoskeletal system, which were not related to the application of the vaccine viruses. Therefore, the animals were euthanized at different time points prior to the proposed end of the study.

One of the animals aborted at 54 days after the infection. All fetuses, including the aborted one, were found normal by weight and development. No pathological findings were recorded at necropsy.

Virus isolation in cell culture was performed from 0.3 g of organ material (shock frozen, ground with sea sand) followed by 1 consecutive passage of the supernatants in case of first negative results.

Virus isolation was conducted on MDBK cells and on interferon-incompetent MDBK cells. Immunofluorescence analyses of the cultures showed no staining for BVDV. 1 ml of a questionable bone marrow lavage sample was also inoculated on 7 cm$^2$-tissue culture plates. Even after 3 additional passages, the cultures were negative for virus replication.

Fetal tissues were screened for the presence of BVDV proteins with a commercial antigen ELISA (BVDV Ag/Serum plus, Idexx Europe B.V.). Skin, kidney, tonsils, serum, as well as leukocytes, were tested clearly negative for BVDV-antigen. Fetal organs and tissues were also subjected to real-time RT-PCR analyses. After disruption and homogenisation of the samples with a TissueLyser®, RNA was extracted from kidney, cerebellum, leukocytes and thymus with the RNeasy®mini kit (Qiagen) according to the instructions given by the manufacturer. No viral genome equivalents were detected in a subsequent highly sensitive real-time RT-PCR [Hoffmann B, Depner K, Schirrmeier H, Beer M. A universal heterologous internal control system for duplex real-time RT-PCR assays used in a detection system for pestiviruses. J Virol Methods. 2006; 136(1-2):200-209].

Conclusion

In conclusion, it could be clearly demonstrated that the intravenous/intranasal or the intramuscular application of high titers of the BVDV mutant CP7ΔNpro was innocuous for cattle also during early pregnancy. Neither clinical signs of the heifers nor persistent infection of the fetuses could be observed. Despite the fact, that it remains unclear, whether the CP7 Npro deletion mutant was actually able to cross the placental barrier or if the fetuses were able to clear the infection with CP7ΔNpro, no infectious virus was re-isolated from a large panel of fetal organs. In addition, no virus genomes could be detected in purified blood leukocytes and numerous organs of the fetuses. No fetopathogenic effects were observed upon infection of pregnant heifers in the first trimester of gestation with the modified live virus CP7 ΔNpro. In summary, the experimental infection of pregnant heifers gives good evidence, that CP7ΔNpro is a highly attenuated and safe BVDV vaccine candidate.

The invention claimed is:

1. An attenuated, mutant cytopathogenic pestivirus, in which part of the gene sequence encoding the Npro region is deleted, but in which the coding sequence for the N-terminal twelve amino acids of the Npro protein is retained, having an intact Erns gene and expressing all structural proteins of the virus, wherein the cytopathogenic pestivirus is selected from the group consisting of Bovine Viral Diarrhea Virus (BVDV), Classical Swine Fever Virus (CSFV) and Ovine Border Disease Virus (BDV).

2. A mutant according to claim 1, wherein the pestivirus is Bovine Viral Diarrhea Virus (BVDV).

3. The mutant according to claim 1, wherein all of the Npro gene sequence, except for the coding sequence for the N-terminal twelve amino acids of the N-pro protein, is deleted.

4. The mutant according to claim 2, wherein the N-terminal twelve amino acids of the Npro protein are MELITNEL-LYKT- [SEQ ID NO.: 5].

5. The mutant according to claim 4, wherein the pestivirus is BVDV strain CP7.

6. A vaccine for the protection of cattle against BVDV infection comprising an immunogenically protective amount of a mutant pestivirus according to claim 1 and a pharmaceutically acceptable carrier.

7. The vaccine according to claim 6, wherein the mutant is based on the CP7 BVDV strain, wherein all of the Npro gene, except for the coding sequence for the N-terminal twelve amino acids of the Npro protein, is deleted.

8. A method for protecting a bovine animal against BVDV infection comprising administering an effective amount of the vaccine according to claim 6.

9. The method of claim 8, wherein the bovine animal is a pregnant heifer.

* * * * *